United States Patent
Cherek et al.

[19]

[11] Patent Number: 6,112,254
[45] Date of Patent: Aug. 29, 2000

[54] METHOD OF DETECTING CHARACTERISTICS OF LIQUIDS IN PIPES AND PUMP CONTROLLING

[75] Inventors: Bogdan Cherek; John Joseph Lee, both of Peterborough, Canada

[73] Assignee: Milltronics Ltd., Peterborough, Canada

[21] Appl. No.: 09/011,136

[22] PCT Filed: Aug. 2, 1996

[86] PCT No.: PCT/CA96/00521

§ 371 Date: Jul. 30, 1998

§ 102(e) Date: Jul. 30, 1998

[87] PCT Pub. No.: WO97/06433

PCT Pub. Date: Feb. 20, 1997

[30] Foreign Application Priority Data

Aug. 3, 1995 [GB] United Kingdom .................. 9515964

[51] Int. Cl.[7] ............................ G01N 11/00; G06F 13/00
[52] U.S. Cl. ........................ 710/1; 73/54.02; 73/54.41; 73/592; 73/596; 340/603
[58] Field of Search .................... 710/1; 340/603; 73/54.41, 592, 596, 861.04, 54.02

[56] References Cited

U.S. PATENT DOCUMENTS

| | | | |
|---|---|---|---|
| 4,203,324 | 5/1980 | Baumoel | 73/290 V |
| 4,386,409 | 5/1983 | Petroff | 702/48 |
| 4,543,817 | 10/1985 | Sugiyama | 73/40.5 A |
| 4,879,088 | 11/1989 | Swam et al. | 376/252 |
| 5,038,614 | 8/1991 | Bseisu et al. | 73/592 |
| 5,115,672 | 5/1992 | McShane et al. | 73/596 |
| 5,215,706 | 6/1993 | Cross et al. | 376/252 |
| 5,271,267 | 12/1993 | Baumoel | 73/54.41 |
| 5,415,048 | 5/1995 | Diatschenko et al. | 73/861.04 |
| 5,455,565 | 10/1995 | Moeenziai et al. | 340/603 |

*Primary Examiner*—Thomas C. Lee
*Assistant Examiner*—Tammara Peyton
*Attorney, Agent, or Firm*—Ridout & Maybee

[57] ABSTRACT

In order to determine the nature of fluid passing through a pipe, for example whether material being pumped through a pipe is sludge or liquid phase, high frequency ultrasonic pulses from a generator are caused to propagate around a peripheral wall of the pipe to produce ringing in the pipe, and the characteristics of the ringing are measured and compared in a controller with stored data to determine the nature of the fluid content of the pipe. A sludge pump may be controlled according to whether the data obtained shows that the material passing through the pipe is sludge or liquid tunnelling through the sludge.

6 Claims, 4 Drawing Sheets

METHOD OF DETECTING CHARACTERISTICS OF LIQUIDS IN PIPES AND PUMP CONTROLLING

This invention relates to the detection of density and consistency changes in liquids, more particularly although not exclusively sludges in waste water plants, and extends to the control of pumping equipment responsive to such detection.

In the treatment of waste water, the pumping of sludges is extensively used to transfer such sludges between stages in the treatment process, and maintenance of correct sludge densities is critical to the proper operation of certain stages of treatment. Under static conditions, there is a tendency to separation into sludge and aqueous phases, and in pumping from a body in which such separation has occurred, there is a tendency for the aqueous phase to 'tunnel' through the sludge and be pumped preferentially to the sludge. In some circumstances also, sludge density may become excessive. This makes it difficult to maintain a correct sludge density in a destination vessel, but we are not aware of any means currently available that will detect reliably the density of sludge being pumped by a sludge pump. Similar problems arise in other applications where liquids having mixed phases or variable density are being pumped.

Attempts have been made to detect sludge density by acoustic methods, but problems have arisen as a result of pump noise, unpredictable responses of pipework associated with pumps, and very high acoustic absorbtion by typical sludges.

Proposals have also been made in U.S. Pat. No. 4,145,917 to measure the properties of liquid in a vessel by applying a transducer to the wall of a vessel to project pulses ultrasonic energy into a liquid, and measuring characteristics of the response to these pulses.

It has now been found that a predictable, reliable and rapid detection of the nature of liquid in pipework associated with pumps can be achieved utilizing ultrasonic techniques.

According to the invention, there is provided a method of detecting changes in nature of liquid in a vessel, by applying pulses of ultrasonic energy to the vessel, in which the vessel is a pipe, the pulses are applied to a wall of the pipe to propagate therearound, sensing ringing of the pipe wall responsive to such propagation, analyzing at least one parameter of said ringing to determine a signature found to be modified according to the nature of liquid within the pipe, and comparing the signature so obtained with stored data to determine the nature of said liquid, the frequency of the ultrasonic energy being sufficiently high that its wavelength is small compared with the cross-sectional dimensions of the pipe and that it lies above a spectrum of noise associated with pumping.

The invention also extends to methods for controlling pumps operating upon liquids subject to "tunnelling", or other instructions of unwanted phase or density anomalies.

Further features of the invention will be apparent from the following description with reference to the accompanying drawings, in which.

Figure 2:
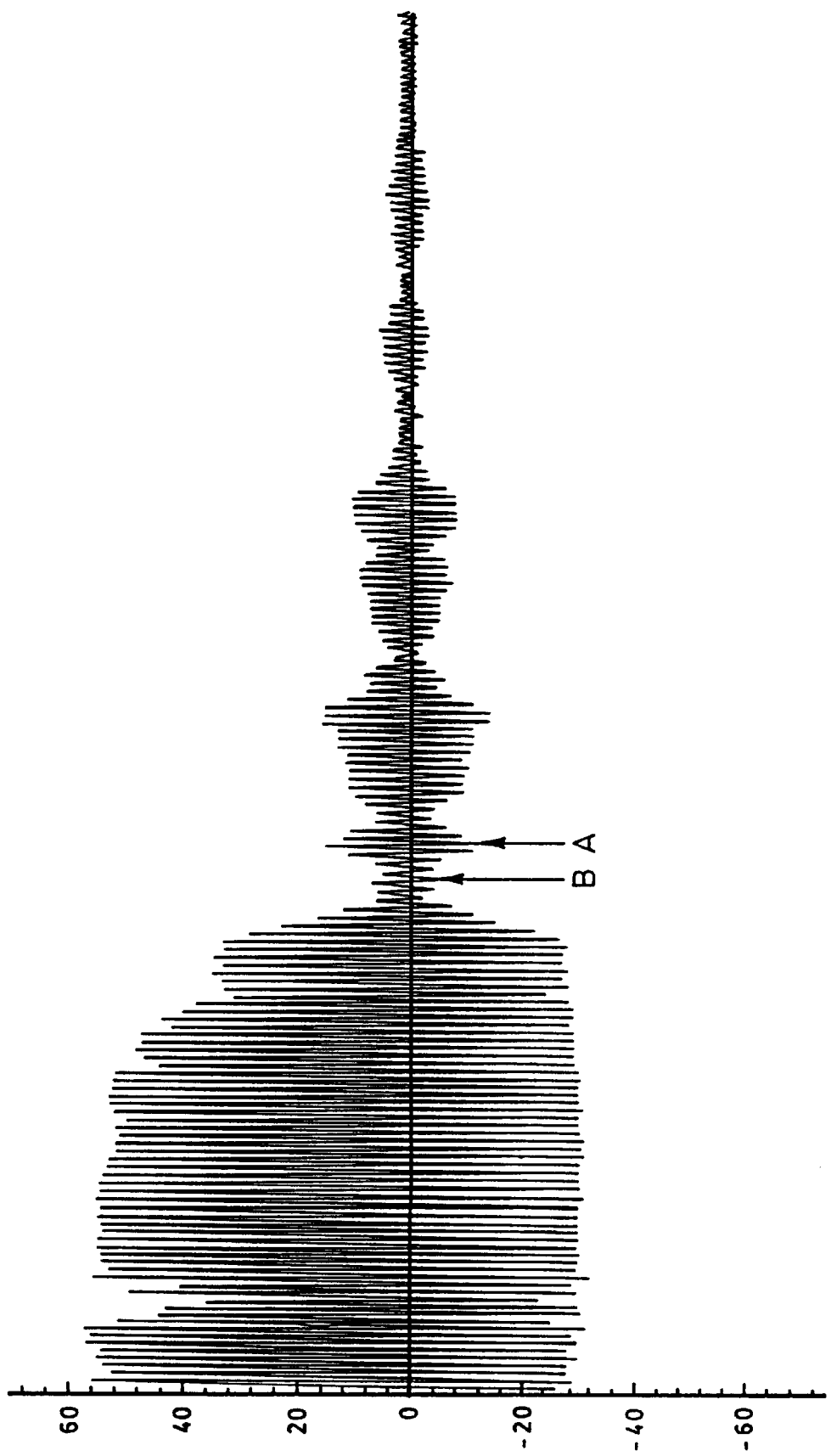
FIGS. 2 and 3 are plots of the response obtained from a particular installation responsive to changes in liquid density of sewage sludge.

Referring to FIG. 2, two high frequency ultrasonic transducers 2 and 4, having an equal resonant frequency typically of about 150 kHz, are applied to opposite sides of an entry pipe 6 to a pump 8 in a waste water treatment plant by means of housings 10 and 12 which may be attached to the pipe by magnets 14 or clamps. Although two separate transducers are shown, respectively for applying ultrasonic energy to the pipe and for picking up the response, a single transducer could be utilized, with suitable provision to isolate receiver circuits associated with the transducer from transmitter circuits, similar to that provided in other ultrasonic applications using a common transducer both for transmitting and receiving ultrasound.

The transmitter transducer 2 is pulsed by a pulse generator 16, which in the example shown generates a single 2000 volt peak-to-peak pulse of 1 microsecond duration, at intervals sufficiently spaced for control of the resulting ringing of the pipe coupled to the transducer to be monitored to provide desired data, as described further below. In practice, in a typical installation, up to 50 or more pulses per second are possible, but a considerably smaller number, for example 10 per second, will provide adequate control information. In the embodiment shown, the pulse generator, which may be of any suitable type providing a desired pulse amplitude and duration, is controlled by a microcontroller 18 which also controls the processing of signals received from the receiver transducer 4, which signals are applied to a preamplifier 20 tuned to the resonant frequency of transducers, and providing an output at a suitable level for further processing. The preamplifier 18 typically includes a detector to eliminate the 150 kHz carrier component, and provides an output which is digitized by an analog to digital converter. The detector may be a simple amplitude detector, but a phase detector may be preferred to extract additional information from the signal, particularly as to the positions of zero crossings. The analog to digital converter may be implemented in the microcontroller 18 as may interfaces to the pulse generator 16 and to a relay 22 connected to a pump control circuit 24.

It is found that the amplitude of the output from the receiver transducer is strongly influenced by the nature and density of the liquid in the pipe 6, while the resonant frequency of the transducers is high enough to avoid interference from noise generated by the pump 8. The wavelength of the ultrasonic energy produced, typically of the order of a few centimeters, is small compared to the cross sectional dimensions of the pipe, which therefore does not act as a waveguide for the energy. the energy propagates largely around the wall of the pipe, subject to a degree of coupling with the pipe contents which is dependent upon the nature and density of the later, as illustrated by the traces of FIGS. 2 and 3, which illustrate preamplified signals from the transducer 4 in an installation similar to that of FIG. 1.

Figure 3:
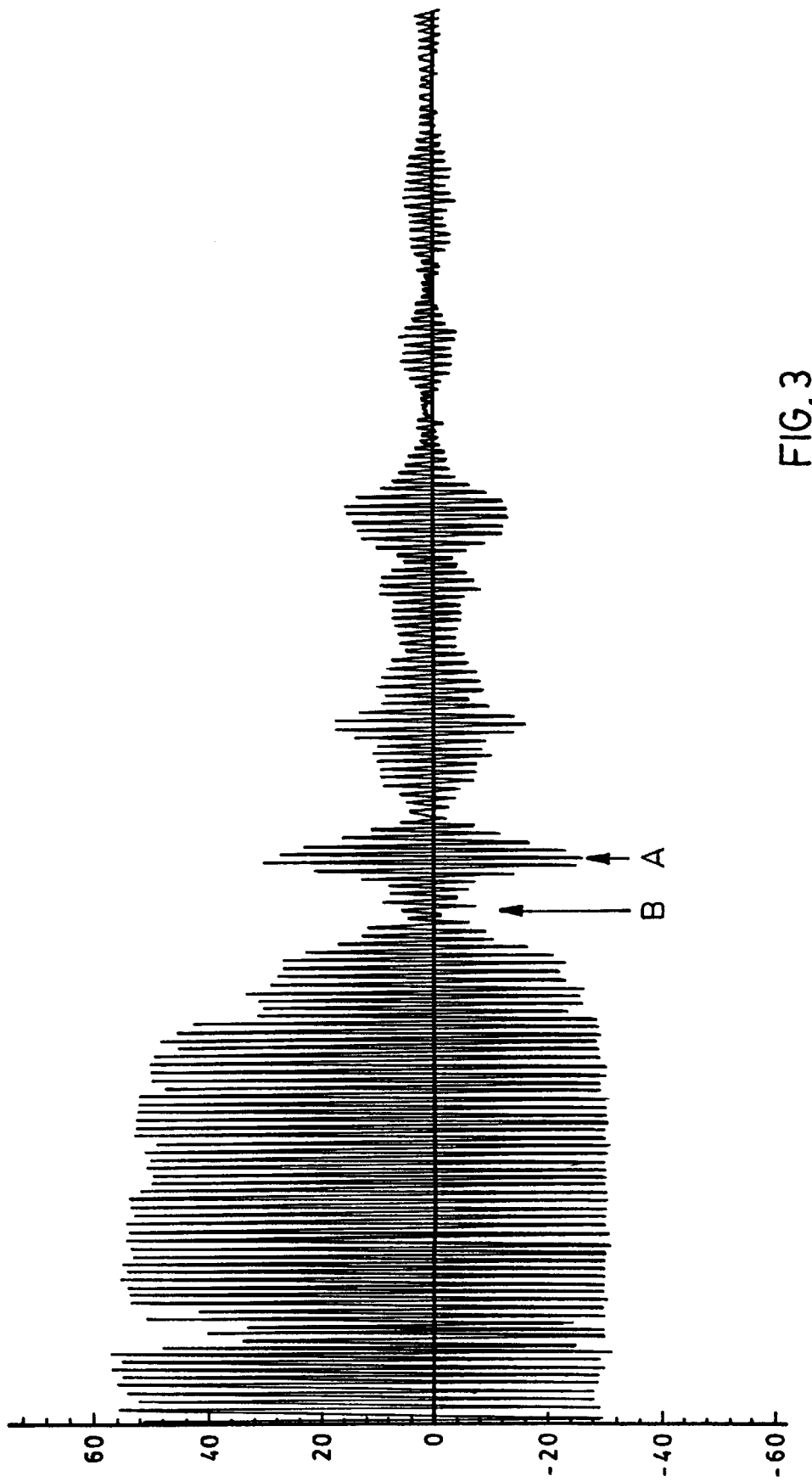

After an initial period following the pulse, in which the peak amplitude is largely governed by saturation effects in the preamplifier (although a minimum will be noted in FIGS. 2 and 3 near the start of each trace), the amplitude of the ringing of the transducer and the pipe to which it is coupled is characterized by a number of peaks and valleys following a similar pattern in each trace, although the amplitudes of most of the peaks are greater in FIG. 3, corresponding to a higher density of the liquid in the pipe. It will be noted that the amplitudes of the various peaks are affected to different degrees, pointing to a change in the spectral content of the envelope signal. Surprisingly, is found that, with sewage sludge, coupling into the liquid decreases with increasing density of the sludge resulting in lager peaks, but this is not necessarily characteristic of other liquids, and individual calibration and selection of signature features is necessary to optimize differentiation between particular liquids of different natures and densities.

The digitized signal is analyzed as discussed further below, and in the example shown is translated into a signal proportional to sludge density which is compared with stored signals corresponding to maximum and minimum permissible densities. Depending on the results of this comparison, the relay 22 is operated to control the pump circuit 24 associated with the pump 8. Thus the system may be set up so that the pump 8 is topped if the signal corresponding to the density of the liquid moves outside the thresholds represented by the stored signals. A drop in density indicates that tunnelling may be occurring in the body of liquid from which the pump draws its input or that available sludge has been pumped. A rise in density above the upper threshold indicates that the sludge being pumped is too dense: it may not in all cases be necessary to monitor an upper threshold if overdense sludge is not a problem. Once the sensed liquid density is again within the thresholds, the pump is restarted. Since the liquid density in the inlet pipe may not automatically be restored when pumping ceases, the microcontroller 18 will control the relay to restart the pump after a time lapse considered sufficient to stop tunnelling or similar phenomena but it will again stop the pump if the density in the pump inlet pipe is not restored within a further interval as pumping continues. By such means, undesirable pumping of low density liquid or high density sludge rather than sludge of correct density can be largely avoided.

Figure 1:
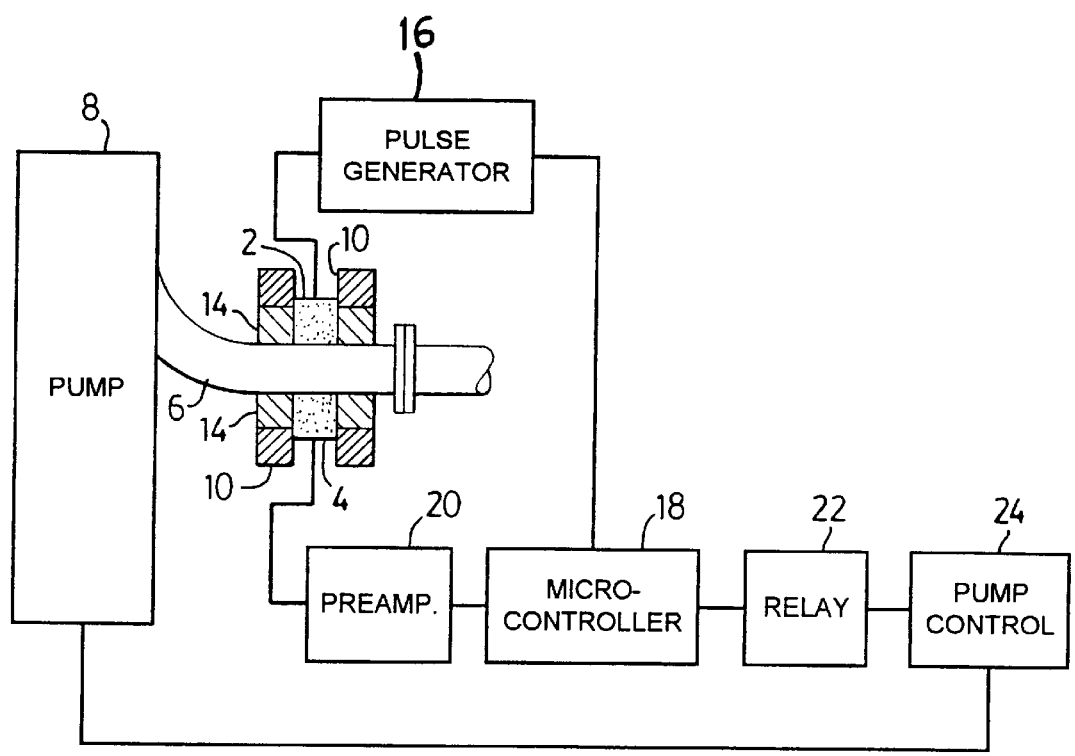
FIG. 1 is a diagrammatic illustration of a typical installation of the invention.

It is found that the influence of the location of coupling of the transducer or transducers to the pipe is not very marked, and the same applies to the layout of the pipework associated with the pump, although it is found that a position on an elbow, such as an elbow at the entrance to the pump (as shown in FIG. 1), is advantageous since the flow through such an elbow tends to prevent solids build up on the wall of the pipe. Such build up may also be inhibited by the ultrasonic pulsing itself.

Figure 4:
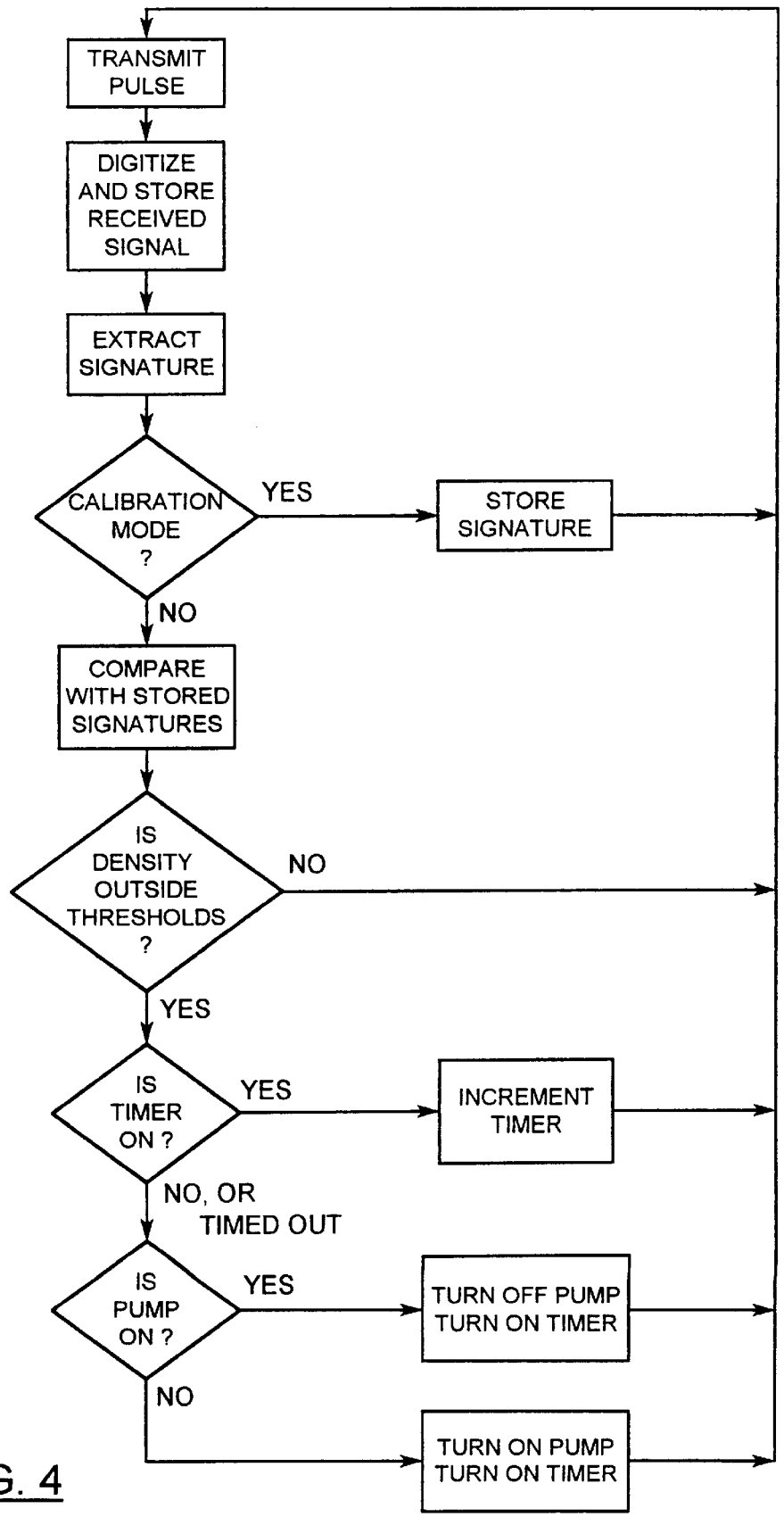
FIG. 4 is a simplified flow diagram illustrating processing of signals in an embodiment of the invention.

In use, the microcontroller is controlled by a program routine similar to that outlined in FIG. 4. It should be appreciated that the microcontroller may control other aspects of pump operation, for example levels in reservoirs upstream and/or downstream of the pump, so that the routine shown will only be part of the overall control program of the microcontroller. It may for example be implemented as an interrupt service routine called by a timer integrated into the microcontroller at intervals determined by a desired pulse repetition frequency selected to provide a desired rapidity of response to density fluctuations. It may also be desired to base density calculations on the averaged response to multiple pulses so as to provide greater noise/immunity, which in turn will require a higher repetition frequency for the same speed of response.

The routine of FIG. 4 starts by triggering the pulse generator 16 to transmit a pulse to the transducer 2, and then activates the analog-to-digital converter to digitize and store the detected signal from the preamplifier 20, possibly discarding an initial portion of the signal so as to disregard that portion of the response during which the preamplifier is saturated. The stored digitized signal is then analyzed to recognize components of the detected signal which characterize the type and density of the liquid in the pipe.

This analysis can take various forms, but in each case may be considered to constitute recognition in the received signal of a signature characterizing the nature of the liquid in the pipe 6. In one simple technique, the amplitude of the peak A (see FIGS. 2 and 3) immediately following a first zero-crossing B in the detected signal is determined; the amplitude of this peak varies markedly with relatively small changes in sludge density, as will be seen by comparison of FIGS. 2 and 3, which show the response to sludges having densities of 1.031 and 1.0342 respectively. More sophisticated techniques may examine the amplitude of several peaks in the response, or analyze the response in the frequency domain to measure the relative amplitudes of different frequency components in the response after detection. Using phase detection, either or both real and quadrature components of the response may be analyzed. Another approach is to integrate the amplitude response over a defined interval after the preamplifier has ceased to be saturated. The approach taken in any particular application will depend upon the data required. For example, where it is merely desired to determine whether the density of a particular sludge being pumped falls within a predetermined response density range, it may be sufficient to determine that the amplitude of peak A falls within a specific range of amplitude determined during a calibration phase. In other applications, it may be necessary to extract a signature comprising more parameters of the response, and compare or pattern match this signature with a signature or signatures stored during a calibration phase so as to determine the density or nature of liquid in the pipe, for example whether it is water or oil. In each case, the response to different liquids is studied, with a view of measuring those features or combinations of features of the response which will provide a signature best adapted to differentiate the liquids to be detected.

Calibration uses a similar routine to that utilized during normal use, except that the pipe is supplied with liquid of known density and nature, and the signature obtained is stored for use in future comparisons, rather than itself being compared to stored values.

The method of the invention may be extended to provide control of pumping of liquid in the pipe as described above; a simple version of such a control function is included in the diagram of FIG. 4.

What is claimed is:

1. A method of detecting the nature of liquid in a vessel, comprising applying pulses of ultrasonic energy to the vessel and examining the response thereto, wherein the vessel is a pipe, the pulses are applied to a wall of the pipe to propagate therearound, sensing ringing of the pipe wall responsive to such propagation, analyzing at least one parameter of said ringing to determine a signature found to be modified according to the nature of liquid within the pipe, and comparing the signature so obtained with stored data to determine the nature of said liquid, the frequency of the ultrasonic energy being sufficiently high that its wavelength is small compared with the cross-sectional dimensions of the pipe and that it lies above a spectrum of noise associated with pumping.

2. A method according to claim 1, wherein the ringing is detected, digitized and stored prior to analysis.

3. A method according to claim 2, wherein the signature is the amplitude of the first peak in the ringing following a first zero crossing, and that the liquid in the pipe is sewage sludge.

4. A method of controlling a pump moving liquid through a pipe, which comprises applying the method of claim 1 to compare the signature of liquid in the pipe with a threshold determined by stored data, and stopping the pump when the signature falls outside the threshold.

5. A method of controlling a pump according to claim 4, wherein the pump is restarted when the signature again falls within the threshold, or after a predetermined time lapse, whichever occurs first.

6. A method according to claim 4, wherein the ringing is detected, digitized and stored prior to analysis, and the signature is the amplitude of the first peak in the ringing following a first zero crossing, the liquid in the pipe being sewage sludge.

* * * * *